United States Patent [19]
Lonardo

[11] Patent Number: 5,275,179
[45] Date of Patent: * Jan. 4, 1994

[54] METHOD FOR PREVENTING SKIN ABRASIONS FOR PATIENTS HAVING LEGS SUBSTANTIALLY LOCKED IN JUXTAPOSITION

[75] Inventor: Robert Lonardo, Treasure Island, Fla.

[73] Assignee: L'Nard Associates, Inc., Clearwater, Fla.

[*] Notice: The portion of the term of this patent subsequent to May 22, 2007 has been disclaimed.

[21] Appl. No.: 677,157

[22] Filed: Mar. 29, 1991

Related U.S. Application Data

[63] Continuation of Ser. No. 306,808, Feb. 3, 1989, which is a continuation of Ser. No. 107,980, Oct. 14, 1987, abandoned.

[51] Int. Cl.$^5$ .................................. H61F 5/30
[52] U.S. Cl. ..................... 128/882; 128/881; 128/892
[58] Field of Search ............ 128/881, 889, 892, 894, 128/882, 869, 894, 85, 878

[56] References Cited

U.S. PATENT DOCUMENTS

| | | | |
|---|---|---|---|
| 2,606,554 | 8/1952 | Simon | 128/881 |
| 3,911,497 | 10/1975 | Lewis, Jr. et al. | 128/892 X |
| 4,736,477 | 4/1988 | Moore | 128/892 X |
| 4,922,929 | 5/1990 | De Journett | 128/892 |
| 4,953,569 | 9/1990 | Lonardo | 128/892 |

Primary Examiner—Robert A. Hafer
Assistant Examiner—Brian F. Hanlon
Attorney, Agent, or Firm—Zarley, McKee, Thomte, Voorhees, & Sease

[57] ABSTRACT

A flexible planar pad having a top, bottom, side edges, and opposite leg engaging surfaces. The leg engaging surfaces comprises a soft resilient material so that the skin and flesh of the inner portion of a patient's legs will be protected from abrasive action. A first strap means is secured to the pad adjacent its upper end for securing the pad to a patient's leg just above the knee. A second strap means is secured to the pad adjacent the bottom thereof for securing the pad to the patient's leg just above the ankle. A third strap means can be used alternately and it is secured to the pad just below the knee portion to again secure the pad to the leg of the patient just below the knee.

1 Claim, 2 Drawing Sheets

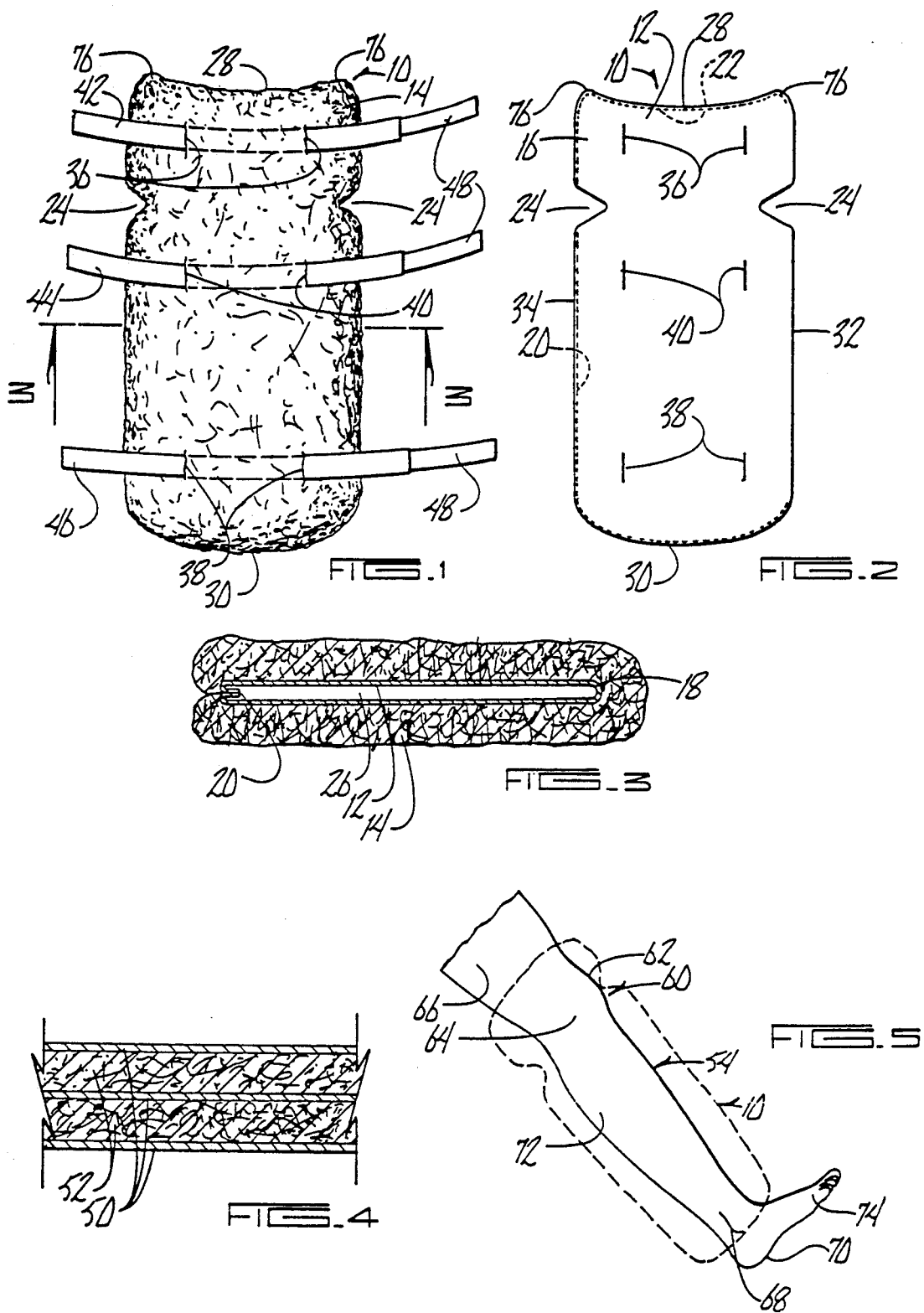

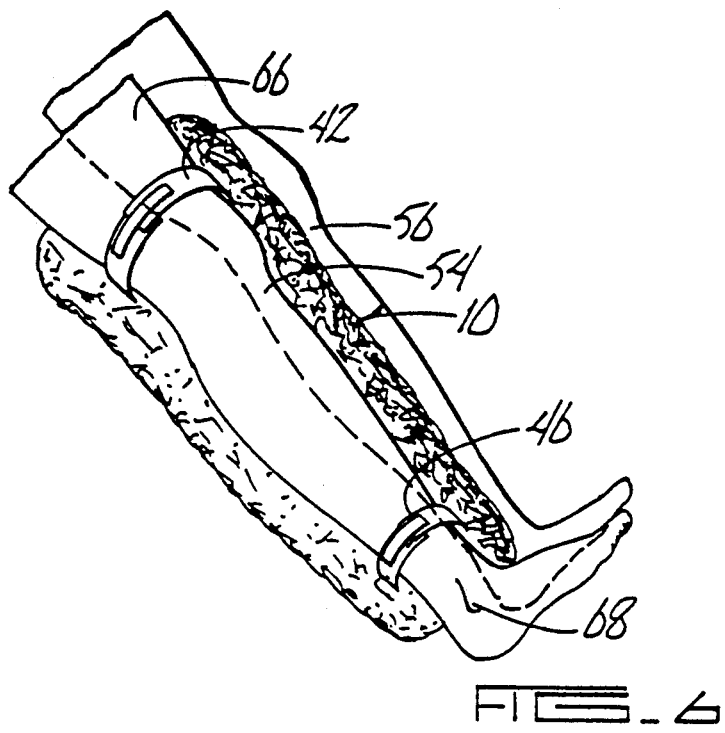
FIG_6
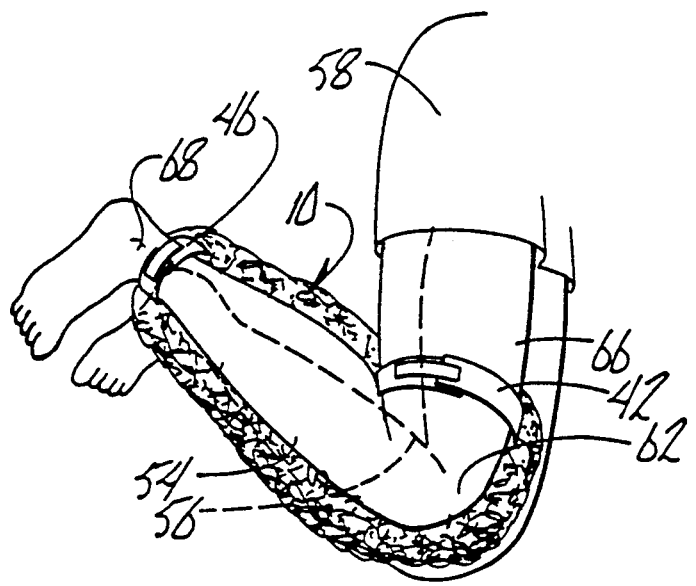
FIG_7

METHOD FOR PREVENTING SKIN ABRASIONS FOR PATIENTS HAVING LEGS SUBSTANTIALLY LOCKED IN JUXTAPOSITION

This application is a continuation of application Ser. No. 306,808, filed Feb. 3, 1989 which is a continuation of application Ser. No. 107,980, filed Oct. 14, 1987 now abandoned.

BACKGROUND OF THE INVENTION

Many bedridden patients, usually paralysis victims, have their legs substantially locked together in close juxtaposition. This condition is known as valgus wherein the muscles of the hip contract so that the legs cannot be spread. Such patients normally lay on their sides in a fetal position. Skin abrasions, sores and ulcers often are created at the knees, ankles and feet where the non-muscular portions of the legs tend to more forcibly engage. Slight movement of either leg aggravates this situation.

Pillows or the like are often forcibly inserted between such a patient's legs. However, pillows are often of improper thickness, and do not stay in place.

Therefore, a principal object of this invention is to provide a method and means for preventing skin abrasions for patients having legs substantially locked in juxtaposition which will prevent abrasion between the patient's legs as they bear against each other.

A further object of the invention is to provide a method and means for preventing skin abrasions for patients having legs substantially locked in juxtaposition which will prevent abrasion between the patient's legs as they bear against each other, and which will maintain this protection regardless of patient movement.

A still further object of this invention is to provide a means for preventing skin abrasions for patients having legs substantially locked in juxtaposition which is easily attached to the patient.

A still further object of this invention is to provide a means for preventing skin abrasions for patients having legs substantially locked in juxtaposition which is comfortable to the patient.

A still further object of this invention is to provide a means for preventing skin abrasions for patients having legs substantially locked in juxtaposition which can be easily removed, cleaned and reused.

A still further object of this invention is to provide a means for preventing skin abrasions for patients having legs substantially locked in juxtaposition which will not interfere with the blood circulation in the patient's legs.

A still further object of this invention is to provide a means for preventing skin abrasions for patients having legs substantially locked in juxtaposition which will only partially encompass one of the patient's legs to keep the leg from becoming unduly warm.

A still further object of this invention is to provide a means for preventing skin abrasions for patients having legs substantially locked in juxtaposition which can be used on either leg of the patient.

These and other objects will be apparent to those skilled in the art.

SUMMARY OF THE INVENTION

The method of this invention pertains to preventing skin abrasions and the like in patients whose legs are substantially locked together in juxtaposition. The method comprises the taking of an elongated flexible planar pad with a length extending from above the patient's knees to the bottom of the patient's foot. The width of the pad is approximately one-half of the girth of one of the patient's legs. The pad is placed between the patient's legs so that the opposite sides of the pad cover the inner surface of at least one leg from a point above the knee to a point substantially to the bottom of the foot of one leg. The pad is affixed to one leg of the patient at points above the knee and above the ankle of one leg to hold the pad against any substantial movement with respect to the one leg.

The apparatus of this invention comprises a pad for the foregoing method. The pad is a flexible planar pad having a top, bottom, side edges, and opposite leg engaging surfaces. The leg engaging surfaces comprise a soft resilient material so that the skin and flesh of the inner portion of a patient's legs will be protected from abrasive action. A first strap means is secured to the pad adjacent its upper end for securing the pad to a patient's leg just above the knee. A second strap means is secured to the pad adjacent the bottom thereof for securing the pad to the patient's leg just above the ankle. A third strap means can be used alternately and it is secured to the pad just below the knee portion to again secure the pad to the leg of the patient just below the knee.

The pad is formed by a layer of canvas material to which is affixed the soft resilient material which forms the padding thereof. The canvas material is folded along a central seam, and the outer periphery of the overlapped portions of the pad are then sewn together.

Opposite notch elements are cut into the pad at the side edges towards the upper portion thereof. These notched edges are not sewn and form an access to the interior compartment of the pad.

The strap means are threaded through opposite pairs of vertical slots in one surface of the pad.

The upper portion of the pad is formed in a downwardly extending concave shape, and the bottom of the pad is formed in a downwardly extending convex shape.

BRIEF DESCRIPTION OF THE DRAWINGS

FIG. 1 is a plan view of the pad of this invention;

FIG. 2 is a plan view of the pad of this invention during an initial stage of fabrication with the strap elements omitted therefrom;

FIG. 3 is an enlarged scale sectional view taken on line 3—3 of FIG. 1;

FIG. 4 is a partial sectional view at an enlarged scale taken through one of the strap elements;

FIG. 5 is an elevational view of one leg of a patient;

FIG. 6 is a partial perspective view of the opposite side of the leg shown in FIG. 5 with the pad attached thereto; and FIG. 7 is a perspective view of the pad of this invention affixed to the leg of a patient in a position different than that of FIG. 6.

DETAILED DESCRIPTION OF THE PREFERRED EMBODIMENT

The numeral 10 designates the pad of this invention which is comprised of canvas layer 12, with a soft resilient padding material 14 secured to one surface thereof. The material 14 is a washable polyester fiber having the texture of wool fleece and is available under the trademark "Kodel". The pad 10 is symmetrically cut about a center fold 16 and is thereupon folded on both center folds 16 and fold 18 into the configuration shown in FIG. 2. At that stage of the fabrication, the canvas layer 12 is on the outside. The lower portion of the pad is then secured together by sewn seam 20. The pad is then turned inside out so that the material 14 appears on the outside thereof, and seam 22 is then put in place to substantially enclose the interior of the pad.

V-shaped notches 24 are cut in opposite sides of the pad near the top thereof. The notches are not sewn closed and serve as access to the interior compartment 26 of the pad. Access to the interior compartment 26 is desirable as will be described hereafter.

The pad 10 includes a top 28 which has a concave shape that extends downwardly, and a bottom 30 which has a convex shape which also extends downwardly. The numerals 32 and 34 designate the side edges of the pad.

A first pair of vertical cuts or slots 36 are located in the upper portion of the pad. A second pair of spaced vertical slots 38 are located towards the bottom portion of the pad; and a third pair of spaced vertical slots 40 are located immediately below the notches 24. A first strap 42 is threaded through slots 36; a second strap 44 is threaded through slots 38; and a third strap 46 can be threaded through slots 40 if it is desired to have a securing means at that point on the leg. The first strap 42 is adapted to secure the pad to the leg immediately above the knee; the second strap 44 is adapted to secure the pad to the leg immediately above the ankle; and the third strap 46, if needed, is adapted to secure the pad to the leg immediately below the knee. It should be noted that the horizontal space between slots 36 is slightly greater than the horizontal space between the lower slots 38 (six inches versus four inches). A conventional Velcro strap 48 is secured to one end of each of the straps and is adapted to fix the free ends of the straps together is conventional fashion.

Each of the straps is comprised of three felt layers 50 (see FIG. 4) which have foam layers 52 interposed therebetween. These straps are soft and are slightly resilient and are intended to be very comfortable to the leg of the patient.

The dimensions for a typical pad 10 adapted for use on an adult are as follows: The vertical height of the pad is approximately 23 inches. The notches 24 are approximately 1½ inches in vertical height, and extend no more than 2¼ inches into the body of the pad from the side edges thereof. The vertical slots described above are approximately two inches in length. The width of the pad at the top is approximately 12 inches, and the width at the lower end is approximately eight inches. The slots 36 are approximately two inches from the top 28, and the slots 38 are approximately two inches from the bottom 30. The first strap 42 is approximately 18½ inches in length and the lower strap 44 is approximately 15 inches in length. The third strap 46, if used, should be approximately 15–18½ inches in length, and preferably closer to 18¼ inches in length. The notches 24 are approximately five inches from the top 28 of the pad. The thickness of the material 14 is approximately three inches, but obviously can be compressed to ¼ inch–¾ inches.

FIGS. 6 and 7 show a patient's legs 54 and 56. With reference to FIG. 5, the numeral 58 designates a patient's thigh; the numeral 60 designates the knee area; the numeral 62 designates the kneecap; the numeral 64 designates the knee joint. The numeral 66 shows the area of the thigh which includes the quadrucep muscle group. The numeral 68 designates the ankle, with the numerals 70, 72 and 74 designating the patient's heel, calf and foot.

The normal operation of the device of this invention is as follows: With at least the straps 42 and 44 attached to the pad, the pad is inserted between the legs 54 and 56 of the patient. The ends of the straps 42 and 44 are secured together just above the knee and just above the ankle as described above by utilizing the Velcro fastener 48. Since the spacing between slots 36 and slots 38 are approximately the "diameter" of the patient's leg at those respective points, the straps pull the pad into close engagement with the leg but do not serve to squeeze the leg so as to impede blood circulation in the leg. With the lower strap 44 being between the ankle and the calf of the leg, and the upper strap 42 being between the knee and the major diameter of the thigh, the pad 10 is held substantially immobile on the leg. However, as slight bending of the knee takes place, the notches 24 permit the lower portion of the pad below the notches to flex freely even though the portion of the pad above the notches and above the knee remain substantially stationary. Preferably, the notches 24 are positioned slightly below the kneecap 62. The corners 76 of the pad serve to maintain padded material between the legs of the patient even though the leg may flex slightly to slightly displace the pad above the knee.

It is important that the lower end or bottom 30 of the pad extend substantially to the medial distal heel to cover all pressure points that might exist between the patient's two legs.

The pad 10 serves to equalize the pressure exerted by the weight or pressure of one leg on the other and relieves the high pressure points between the heels, ankles, and knees of the patient.

The straps of the pad can be washed by removal thereof, and they can be replaced when necessary. This is accomplished by reaching the hand inside the interior of the pad and manipulating the strap out of the vertical slots in which the strap is mounted.

Similarly, the pad can be removed from the patient, laundered, and reused.

Thus, from the foregoing, it is seen that this device will accomplish at least all of its stated objectives.

What is claimed is:

1. A pad for preventing skin abrasions and the like for use between the legs of patients whose legs are substantially positioned in overlapping condition, comprising, a flexible planar pad having a top, bottom, side edges, and opposite uncontoured leg engaging surfaces which are free from preformed indentations, including surfaces to permit simultaneous engagement with opposed heels, ankles and knees of said patient, and having a width sufficient to partially encompass one leg of a patient, said leg engaging surfaces comprising a soft resilient material having the texture of wool fleece so that the skin and flesh of the inner portion of a patient's legs will be protected from abrasive friction when said paid is placed between the legs of a patient whose legs are substantially locked together in overlapping condition, whereby the pressure exerted by the weight of one leg on the other can be equalized and the pressure points between heels, ankles and knees of the patient can be relieved, when said heels, ankles or knees are in overlapping condition, said pad having an empty interior compartment defined by said top, bottom and side edges and opposite leg engaging surfaces, first and second pairs of laterally spaced substantially vertical slots adjacent the top and bottom, respectively, of only one of said leg engaging surfaces, first and second strap means extending through said first and second pairs, respectively, of said first and second pairs of vertical slots, and extending through said interior compartment between the laterally spaced vertical slots of each pair of slots so that said straps will be substantially free from contact with said leg engaging surfaces, and first strap means secured to said pad adjacent the top thereof for securely wrapping said pad partially around a patient's leg above the knee, and a second strap means secured to said pad adjacent the bottom thereof for securely wrapping said pad partially around a patient's leg above the ankle, said first and second strap means adapted to conform the flexible planar pad to the shape of the patient's leg to which it is attached, said first and second strap means extending between said top and bottom of said flexible planar pad so as to be free from contact with the portion of the patient's legs that are normally in contact with each other by reason of said overlapping condition.

* * * * *